United States Patent [19]
Noeske-Jungblut et al.

[11] Patent Number: 5,882,887
[45] Date of Patent: Mar. 16, 1999

[54] PROCESS FOR MANUFACTURE OF A MODIFIED COLLAGEN-INDUCED PLATELET AGGREGATION INHIBITOR PALLIDIPIN

[75] Inventors: Christiane Noeske-Jungblut; Andreas Becker; Bernard Haendler, all of Berlin, Germany

[73] Assignee: Schering Aktiengesellschaft, Germany

[21] Appl. No.: 793,294

[22] PCT Filed: Sep. 11, 1995

[86] PCT No.: PCT/EP95/03573
§ 371 Date: Jun. 16, 1997
§ 102(e) Date: Jun. 16, 1997

[87] PCT Pub. No.: WO96/08563
PCT Pub. Date: Mar. 21, 1996

[30] Foreign Application Priority Data

Sep. 12, 1994 [EP] European Pat. Off. .............. 94250224

[51] Int. Cl.$^6$ ........................ C07K 14/44; C07K 14/475; C12N 15/30; A61K 38/17
[52] U.S. Cl. .................. 435/69.1; 435/69.8; 435/252.33; 435/320.1; 435/476; 514/12; 514/822; 530/350; 536/23.5
[58] Field of Search .................................. 435/69.7, 69.8, 435/172.3, 252.3, 320.1, 69.1, 476, 252.33; 514/2, 12, 822; 530/350, 858, 412; 536/23.5

[56] References Cited

U.S. PATENT DOCUMENTS 5,723,312   3/1998   Noeske-Jungblut ................... 435/69.1

OTHER PUBLICATIONS

Chan, B.M.C. et al. *Science* 251:1600–1602 (1991).
Chelberg, M.K. et al. *J. Cell Biology* 111:261–270 (1990).
Becker, R.C. et al. *Science & Medicine* Jul./Aug. 1996, pp. 12–21.

*Primary Examiner*—Dian C. Jacobson
*Attorney, Agent, or Firm*—Miller, White, Zelano, & Branigan, P.C.

[57] ABSTRACT

The invention provides a process of manufacture of a recombinant protein called Asp-Pallidipin. Asp-Pallidipin inhibits the collagen-induced platelet aggregation of mammalian platelets. The Asp-Pallidipin comprises (i) a protein (Pallidipin) selected from the group of Pallidipin proteins, and (ii) the amino acid aspartic acid, wherein the aspartic acid is connected by a peptide bond with the N-terminal end of Pallidipin. The process comprises the steps aa) transfecting at least one bacterium with an appropriate vector, wherein the vector comprises:

(i) a DNA or cDNA coding for the recombinant Asp-Pallidipin (ii) a suitable signal peptide sequence which signal sequence is cleaved so that the amino acid aspartic acid is in the position +1 of the amino acid sequence seen from the position of the Pallidipin and (iii) a suitable promoter;

bb) expressing the preprotein comprising Asp-Pallidipin and the signal sequence;

cc) transporting the Asp-Pallidipin from the cytoplasm of the bacterium to the periplasm, cleavage of the preprotein by at least one protease during the transport, producing the Asp-Pallidipin, dd) isolating the Asp-Pallidipin by extracting the periplasm, and ee) purifying the Asp-Pallidipin.

The protein is used as a medicament for inhibiting of collagen-induced human platelet aggregation or of cancer with metastatic tumor cells.

17 Claims, No Drawings

PROCESS FOR MANUFACTURE OF A MODIFIED COLLAGEN-INDUCED PLATELET AGGREGATION INHIBITOR PALLIDIPIN

The invention refers to a process of manufacture of a modified collagen-induced platelet aggregation inhibitor, called Pallidipin. Further the invention comprises the substance Pallidipin which is modified.

Collagen is the most potent inducer known of human platelet aggregation. For instance, upon injury of the vessel wall and exposure to collagen, blood platelets rapidly adhere and become activated. (H. R. Baumgartner (1977) Thromb. Haemostas. 37:1–16; J. Hawiger (1987) Human Pathol. 18:111–122.)

Collagen-induced platelet aggregation of human platelets thus represents a risk factor for patients undergoing blood vessel-affecting procedures, e.g., angioplasty or sepsis, for those suffering myocardial infarction, for those recovering from treatment for myocardial infarction, inter alia.

In some cases it is necessary to inhibit collagen-induced platelet aggregation. Some compounds are known to inhibit such aggregation. For example, synthetic oligopeptides inhibit collagen-induced platelet aggregation by binding to the platelets. See, e.g., Bevers et al. (1985) "Collagen Derived Octapeptide Inhibits Platelet Procoagulant Activity Induced by the Combined Action of Collagen and Thrombin", Thrombosis Research, 37:365–370; Karniguian et al. (1983) "Effect of a Collagen Derived Octapeptide on Different Steps of the Platelet/Collagen Inter-action", Thrombosis Research 32:593–604; Caen et al. (1981) "Oligo-peptides with specific inhibiting properties of collagen-induced aggregation, process for preparing the same and pharmaceutical compositions containing them"; and EPA 0 040 149.

Another source of collagen-induced platelet aggregation inhibitor is an inhibitor identified in a snake venom having an unknown structure. See Smith et al., "Identification of 50 kDalton snake venom proteins which specifically inhibit platelet adhesion to collagen." (1991) FEBS 283:307–310.

A third such inhibitor, from the saliva of a medicinal leech, is described by Munro et al. (1991) "Calin—a platelet adhesion inhibitor from the saliva of the medicinal leech", Blood Coagulation and Fibrinolysis 2:179–184. The publication of the European patent application EP 0 480 651 (Merck & Co. Inc. published 15 Apr. 1992) describes a protein having a molecular weight of about 16 kDalton (kD) and a capacity to inhibit collagen-induced aggregation of human platelets which protein is derived from the salivary gland of the leech *Haemaenteria officinalis*. LAPP is 16 kDa protein from the leech *Haemaenteria officinalis* described in Connolly et al. (1992) J. Biol. Chem. 267:6893–6898. See also Moubatin, described in Waxman and Connolly (1993) J. Biol. Chem. 268:5445–5449.

Yet another type of collagen-induced platelet aggregation is isolatable from insects as described in the European Publication EP 0 530 937. These proteins are designated "Pallidipins".

Alkaline phosphatase (APase) is an *E. coli* protein which is secreted into the periplasmic space. APase is synthesized as a precursor protein, have a 21-amino acid long leader sequence which is clipped off by the leader peptidase in the course of translocation across the bacterial inner membrane into the periplasmic space (Y. Kikuchi et al. (1981) Nucl. Acids Res. 9:5671–5678). Its biosynthesis is regulated by the phosphate concentration of the culture medium, and export of the products of heterologous genes placed downstream of the APase promoter is achieved by using low phosphate concentrations (C. Monteilhet et al. (1993) Gene 125:223–228).

The natural source of Pallidipin protein is limited. Processes using biotechnological methods are a logical solution for manufacturing of Pallidipin. The expression of Pallidipin in baby hamster kidney cells (EP 0 530 937) occurs at a rate of production which should be increased in order to express Pallidipin in industrial amounts. Therefore, an improved system of expression was necessary.

Thus, there was a need for an improved process for the manufacture of recombinant Pallidipin, which inhibits collagen-induced platelet aggregation, and which process has a high yield and allows reproducible isolation of the protein with a high degree of purification. The new process should not negatively affect the biological activity of the resulting Pallidipin protein.

It has now been found that the problem can be solved by a process of manufacture of a recombinant Pallidipin protein (Asp-Pallidipin), wherein the Asp-Pallidipin inhibits the collagen-induced platelet aggregation of mammalian platelets, and wherein the Asp-Pallidipin comprises:

(i) a protein (Pallidipin) selected from the group of Pallidipin proteins, and (ii) the amino acid aspartic acid, wherein the aspartic acid is connected by a peptide bond with the N-terminal end of Pallidipin;

whereby the Asp-Pallidipin has the following amino acid sequences:

a) the sequences indicated in
  aa) SEQ ID NO:1;
  bb) SEQ ID NO:2; or
  cc) SEQ ID NO:3; or b) allelic variants or modifications, or muteins of the sequences in any of the SEQ ID NOS:1 to 3, which allelic variations or modifications or muteins do not substantially affect the activity of the protein, or c) a protein according to any of the SEQ ID NOS:1 to 3 or their variants or muteins mentioned under b) having post-translational modifications which do not substantially affect the activity of the mature protein;

comprising the steps:

aa) transfecting at least one bacterium with an appropriate vector, wherein the vector comprises:
  (i) a DNA or cDNA coding for the recombinant Asp-Pallidipin
  (ii) a suitable signal peptide sequence which signal sequence is cleaved so that the amino acid aspartic acid is in the position +1 of the amino acid sequence seen from the position of the Pallidipin and
  (iii) a suitable promoter;

bb) expressing the preprotein comprising Asp-Pallidipin and the signal sequence;

cc) transporting the Asp-Pallidipin from the cytoplasm of the bacterium to the periplasm, cleavage of the preprotein by at least one protease during the transport, producing the,Asp-Pallidipin, dd) isolating the Asp-Pallidipin by extracting the periplasm, and ee) purifying the Asp-Pallidipin.

*E. coli* is a rapid expression system for the production of heterologous, e.g., eukaryotic, proteins. The incorrect folding of proteins is often a problem during expression of eukaryotic gene products by *E. coli*, which can result in decreased activity of the expression products. The probability of correct folding of the protein is much higher when the protein is transported into the periplasm of the *E. coli* cells than when the protein is maintained in the cytoplasm. Transport of the proteins to the periplasm is induced by signal peptide sequences attached to the mature proteins; these signal peptide sequences together with the mature protein sequences are designated "preproteins". Correct cleavage of the preprotein between the signal peptide sequence and the mature protein is necessary for expression of mature eukaryotic proteins in *E. coli*; the sequence of the signal sequence and the sequence of the mature protein have an influence on the correct cleavage. Therefore, not all signal peptide sequences are compatible with all coding sequences.

The *E. coli* alkaline phosphatase signal sequence is known to be effective for the export of preproteins. But it is known that the combination of a given signal peptide sequence and a sequence of a mature protein will not necessarily result in good processing of the preprotein.

Surprisingly, it has been found that the yield of the inventive process of manufacture is 15 times higher than the yield of the expression system using the baby hamster kidney cells. These results are shown in the Examples. The function and activity of the Asp-Pallidipin, as compared with the eukaryotic hamster kidney expression system, is not negatively affected by the inventive process. A further advantage is that the protease (e.g., leader peptidase) necessary for the cleavage of the preprotein is produced by *E. coil* itself.

Purification of the mature Asp-Pallidipin is much easier using the inventive process than is purification of expressed proteins produced and stored within the cytoplasm of the bacterium. Osmotic shock is sufficient to release the Asp-Pallidipin accumulated in the periplasm.

In a preferred embodiment, the DNA encoding the signal peptide sequence codes for the signal sequence of alkaline phosphatase (APase), preferably *E. coli* APase.

The invention comprises a process wherein the vector for the Asp-Pallidipin of the invention is derived from the vector pSB94 (U. Boidol et al. (1982) Mol. Gen. Genet. 185:510–512).

A further aspect of the invention is a vector as mentioned before and additionally a suitable signal peptide, a suitable promoter and, if need be, a suitable enhancer. Vectors are described in detail in the literature of the Examples and also in the European publications EP 0 480 651; 0 462 632 and 0 173 177.

The bacterium *E. coli* is the preferred host. Other microorganisms are also suitable, e.g., *Bacillus subtilis*.

In addition, the invention comprises a recombinant protein Asp-Pallidipin, wherein the Asp-Pallidipin inhibits collagen-induced platelet aggregation of mammalian platelets, and wherein the Asp-Pallidipin comprises:
  (i) a protein (Pallidipin) selected from the group of Pallidipin proteins, and
  (ii) the amino acid aspartic acid,
  wherein the aspartic acid is connected by a peptide bond with the N-terminal end of the Pallidipin;
whereby the Asp-Pallidipin has an amino acid sequences selected from:
  a) a sequence selected from
    aa) SEQ ID NO:1;
    bb) SEQ ID NO:2; or
    cc) SEQ ID NO:3; or
  b) an allelic variant or modification, or mutein of a sequence of SEQ ID NOS:1 to 3, which allelic variant or modification or mutein has substantially the same activity as the Asp-Pallidipin of SEQ ID NO:1 to 3; or
  c) a protein according to SEQ ID NOS:1 to 3 or their variants or muteins mentioned under b) having post-translational modifications which do not substantially affect the activity of the mature protein.

The invention also comprises a recombinant protein Asp-Pallidipin, wherein the Asp-Pallidipin inhibits collagen-induced platelet aggregation of mammalian platelets, and wherein the Asp-Pallidipin comprises:
  (i) a protein (Pallidipin) selected from the group of Pallidipin proteins, and
  (ii) the amino acid aspartic acid,
  wherein the aspartic acid is connected by a peptide bond with the N-terminal end of the Pallidipin;
whereby the Asp-Pallidipin has the following amino acid sequences:
  a) the sequences indicated in
    aa) SEQ ID NO:1;
    bb) SEQ ID NO:2; or
    cc) SEQ ID NO:3; or
  b) allelic variants or muteins of the sequences in any of the SEQ ID NOS:1 to 3, which allelic variants or muteins do not substantially affect the activity of the protein, or
  c) a protein according to any of the SEQ ID NOS:1 to 3 or their variants or muteins mentioned under b) having post-translational modifications which do not substantially affect the activity of the mature protein;
wherein the Asp-Pallidipin is produced by a process comprising the steps of:
  aa) transfecting at least one bacterium with an appropriate vector,
    wherein the vector comprises an operable linkage of:
      (i) a first DNA or cDNA molecule, encoding recombinant Asp-Pallidipin,
      (ii) a second DNA molecule, encoding a suitable signal peptide sequence, and
      (iii) a suitable promoter;
      whereby, upon expression, the preprotein comprising the signal peptide and Asp-Pallidipin is cleaved so that the amino acid aspartic acid is in the position +1 of the amino acid sequence of the mature Asp-Pallidipin,
  bb) expressing the preprotein comprising the Asp-Pallidipin and the signal peptide sequence;
  cc) transporting the Asp-Pallidipin from the cytoplasm of the bacterium to the periplasm, whereby cleavage of the preprotein by at least one protease during transport produces the mature Asp-Pallidipin,
  dd) isolating the Asp-Pallidipin by extracting the periplasm, and
  ee) purifying the Asp-Pallidipin.

In a further preferred embodiment, the Asp-Pallidipin is produced by a process comprising the steps of:
  culturing a bacterium transfected with an appropriate vector, wherein the vector comprises an operable linkage of:
    (i) a first DNA or cDNA molecule, encoding a recombinant Asp-Pallidipin,
    (ii) a second DNA molecule, encoding a suitable signal peptide sequence, and
    (iii) a suitable promoter;
  whereby, upon expression, the preprotein comprising the signal peptide and Asp-Pallidipin is cleaved so that the amino acid aspartic acid is in the position +1 of the amino acid sequence of the mature Asp-Pallidipin, under conditions whereby the preprotein comprising the Asp-Pallidipin and the signal peptide sequence is expressed, and the Asp-Pallidipin is transported from the cytoplasm of the bacterium to the periplasm, whereby cleavage of the preprotein by at least one protease during transport produces the mature Asp-Pallidipin, and purifying the Asp-Pallidipin from the periplasm.

Preferred is a protein wherein the signal peptide sequence is the signal sequence of alkaline phosphatase (APase), preferably *E. coli* APase.

The industrial application of the proteins of the invention is the use of the proteins as a pharmaceutical composition comprising a protein according to the invention in association with a pharmaceutically acceptable diluent or carrier.

Allelic variations or modifications as mentioned before include alteration in the sequence of the nucleotides or amino acids, alteration of the genotype or phenotype. At least one nucleotide or one amino acid can be substituted, deleted or inserted.

Most deletions, insertions and substitutions in particular, are not expected to produce radical changes in the characteristics of the protein of the invention. Modified or mutated proteins according to the invention can be routinely made and screened in order to determine the exact effect of the substitution, deletion, or insertion, by comparison of the functions of the modified or mutated protein with the characteristic functions of the protein of the invention, e.g., the proteins of SEQ ID NOS:1 to 3, or with the native Pallidipin, thereby determining whether the altered protein has comparable activity, e.g., biological activity.

The genetic code is degenerative; that is, most amino acids are encoded by more than one codon of three nucleotides. Accordingly, allelic variation or modification in the nucleotide sequence may or may not alter the amino acid sequence. Therefore, allelic variations are primarily on the DNA level and may also exist secondarily on the level of the amino acid sequence.

The DNA sequence coding for the protein of the invention can be modified by conventional techniques to produce variations in the final protein of the invention which still has substantially the same activity as the protein of the invention, e.g., the Asp-Pallidipin of SEQ ID NOS:1 to 3, or as compared with the native Pallidipin protein. The activity is measured according to the Examples. Thus, one or more amino acids, for example, 1, 2, 3, 4, 5, 6, 7, 8, 9, 10. . . up to 15 amino acids, can be added, substituted or removed without substantially affecting the activity of the protein of the invention. Substitutions can generally be made in accordance with the following Table 1 when it is desired to modulate finely the amino acid sequence of the protein of the invention.

Substantial changes in function or immunological identity are made by selecting substitutions that are less conservative than those in Table 1, i.e. selecting residues that differ more significantly in their effect on maintaining (a) the structure of the polypeptide backbone in the area of the substitution, for example, as a sheet or helical conformation, (b) the charge or hydrophobicity of the molecule, or (c) the bulk of the side chains.

TABLE 1

NORMAL SUBSTITUTIONS OF AMINO ACIDS IN A PROTEIN

| ORIGINAL RESIDUES | EXEMPLARY SUBSTITUTIONS |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

Muteins are defined by homology between two compared proteins. The expression "homology" comprises similarities of the amino acids and gaps in the sequences of both compared sequences. Similarity of amino acids is defined for example in Table 1. Preferably, the muteins of this invention comprise a sequence of amino acids having a homology of at least 60%, more preferred at least 80%, much more preferred at least 90%, and most preferred at least 95% with the sequence of one of the proteins of SEQ ID NOS:1 to 3.

By "post-translational variations" as mentioned above is meant variations during or after translation, such as formation of disulfide bridges and chemical modifications of amino acids.

Proteins often form covalent intrachain bonds. These disulfide bonds are formed between cysteine-SH amino acids in the folded protein or in the protein which folds during translation. The bonds stabilize the three-dimensional structure of the protein. Such disulfide bonds are rarely formed in protein molecules that are still in the cell cytosol because the high intracellular concentration of the —SS— (disulfide) reducing agent glutathione breaks most of such bonds. Once the proteins are outside the cytoplasm, are secreted or are on the cell surface, they often form additional covalent intrachain bonds.

Furthermore, the amino acids may be altered as described in PCT Application WO 91/10684. Other alterations of the side chains of the amino acids are possible.

The protein of the invention has at least a purity of 40%, preferably at least 60%, more preferably at least 80% and most preferably at least 90%. The purity is defined by the amount of the protein of the invention in relation to the total amount of protein. Using the purification methods described in the Examples, no other proteins other than the proteins of the invention are detectable.

Using the purified protein of the invention, monoclonal antibodies can be produced according to the well-known Koehler and Milstein method which, in particular, comprises conventionally immunizing mice or rabbits with the purified protein of the invention as immunogen, followed by the production of hybridomas from antibody-producing cells of the mouse or rabbit.

The preferred embodiment of the invention is the protein mentioned in SEQ ID NO:1, expressed in *E. coli* strain E 15.

The Asp-Pallidipin exhibits pharmacological activity and may, therefore, be useful as a pharmaceutical. Asp-Pallidipin can be used in a pharmaceutical composition comprising Asp-Pallidipin in association with a pharmaceutically acceptable diluent or carrier. Additionally, the invention comprises a pharmaceutical composition comprising a pharmaceutically active Asp-Pallidipin according to the invention and a pharmaceutically acceptable salt or a pharmaceutically acceptable carrier.

In particular, Asp-Pallidipin inhibits collagen-induced platelet aggregation and inhibits adhesion of tumor cells, preferably of metastatic tumor cells, to collagen.

Asp-Pallidipin inhibits platelet aggregation. The test system is described in the Examples. Asp-Pallidipin significantly inhibits platelet aggregation at a concentration of 0.5 to 50 μg protein. The most preferred Asp-Pallidipin, the protein of SEQ ID NO:1, has an $IC_{50}$ of 50 nmol/L of highly purified protein according to the Examples. Asp-Pallidipin inhibits platelet aggregation at concentrations of from 5 nmol/L to about 1,000 nmol/L.

The results from the in vitro test systems indicate that the proteins of the invention can be used as a medicament or can be used for medical treatment. The test results for the in vitro system can be correlated with the in vivo system, because it is an established system in this field. R. J. Shebuski et al. (1990) Thrombosis and Haemostasis, 64:576–581.

Asp-Pallidipin can be administered by intraperitoneal injections, which can be given daily or at 2 to 3 times a week. When animals receive daily injections to achieve a blood concentration of 100 nmol/L, their platelet aggregation is reduced. No serious side effect are monitored under these conditions. Asp-Pallidipin causes this inhibition of platelet aggregation in mice at daily dosages which achieve a blood concentration of from about 10 nmol/L to 1,000 nmol/L.

Asp-Pallidipin is, therefore, useful for the treatment of atherosclerotic or thrombotic disease lesions or for preventing reocclusion after treatment of myocardial infarction. Asp-Pallidipin can be used as an antiatherosclerotic and antithrombotic agent in mammals, including humans, e.g., to treat atherosclerotic/thrombotic lesions, for example due to rupture of atherosclerotic plaques or those due to perturbation or removal of endothelium, e.g., in sepsis or transplants, or to treat unstable angina. It can also be used to prevent reocclusion after treatment of myocardial infarction by fibrinolysis or by angioplasty (PTCA). If fibrinolytic therapy (with streptokinase, t-PA or other plasminogen activators) is applied to treat myocardial infarction, Asp-Pallidipin can be used as an adjuvant agent to prevent reocclusion of the blood vessel. Treatment of myocardial infarction with a balloon catheter (PTCA) also injures the vessel wall and this may lead to formation of a new thrombus. This can be prevented by administering Asp-Pallidipin during and after the procedure. Asp-Pallidipin can be used in coronary angioplasty as well as in other angioplasty applications.

The invention provides
a) the use of a protein of the invention for manufacture of a medicament for treatment of atherosclerotic or thrombotic disease or for preventing reocclusion after treatment of myocardial infarction (thus, the proteins are useful as prophylactically effective medicaments for treatment of patients known to be at risk of developing a disease or condition);
b) a method of treatment of atherosclerotic or thrombotic disease or for preventing reocclusion after treatment of myocardial infarction, which comprises administration of a disease-suppressing effective amount of the protein of the invention to a patient in need of such treatment;
c) a pharmaceutical composition for treatment of atherosclerotic or thrombotic disease or for preventing reocclusion after treatment of myocardial infarction which comprises a protein of the invention and a pharmaceutically acceptable carrier or diluent.

For these indications the appropriate dosage will, of course, vary depending upon, for example, the compound of the invention employed, the host, the mode of administration and the nature and severity of the condition being treated. However, in general, satisfactory results in animals are indicated to be obtained at daily dosages to achieve a blood concentration of from 10 to 1,000 nmol/L, preferably at daily dosages of from 30 to 300 nmol/L.

The proteins of the invention may be administered by any conventional route, in particular enterally or parenterally, e.g. in the form of injectable solutions or suspensions. Intraperitoneal injection is preferred.

The protein of the SEQ ID NO:1 is the preferred compound.

The present invention provides pharmaceutical compositions comprising compounds of the invention in association with at least one pharmaceutical carrier or diluent. Such compositions may be manufactured in conventional manner. See Remington's Pharmaceutical Science, $15^{th}$ ed. Mack Publishing Company, Easton Pa. (1980).

The proteins of the invention also inhibit adhesion of metastatic tumor cells to collagen. The test system is described in the Examples. The proteins of the invention show a significant adhesion-inhibition of metastatic tumor cells to collagen in a concentration of 1 to 100 μg protein.

The test of the most preferred protein, the protein of SEQ ID NO:1, shows a value of the $IC_{50}$ of 100 nmol/L of the highly purified protein according to the Examples 2 and 15. The proteins of the invention show the adhesion-inhibition of metastatic tumor cells to collagen at concentration of from 10 to 2,000 nmol/L.

The results from the in vitro test systems indicate that the proteins of the invention can be used as a medicament or can be used for medical treatment. The test results can be transferred from the in vitro system to the in vivo system, because it is an established system in this field. Chan et al. (1990), Science, 2:1600–1602.

The proteins of the invention can be administered during and after surgical operations of the primary tumor to prevent formation of metastasis by detached tumor cells which may enter the blood stream during operation. These antimetastatic effects can be demonstrated in an "experimental" and "spontaneous" animal model as described by Chan et al. (1990), Science, 2:1600–1602.

The proteins of the invention can be administered by intraperitoneal injections which are given daily or at 2 to 3 times a week. When animals receive daily injections to achieve a blood concentration of 200 nmol/L, they have a reduced adhesion of metastatic tumor cells measured by counting the value of centers of settled metastatic cells. No serious side effects are noted under these conditions.

The proteins of the invention show this adhesion-inhibition of metastatic tumor cells to collagen in mice at daily dosages to achieve a blood concentration of from 20 to 2,000 nmol/L, preferably concentrations of from 60 to 600 nmol/L.

The proteins of the invention are, therefore, useful for the treatment of cancer; especially cancer with metastatic tumor cells, most preferably cancer with highly metastatic tumor cells.

The invention thus provides
a) the use of a protein of the invention for manufacture of a medicament for treatment of cancer with metastatic tumor cells (the proteins are thus useful for prophylactically effective medicaments administered before, e.g., surgical removal of tumors);

b) a method of treatment of cancer with metastatic tumor cells, which comprises administration of a disease-suppressing effective amount of the protein of the invention to a patient in need of such treatment;

c) a pharmaceutical composition for treatment of cancer with metastatic tumor cells which comprises a protein of the invention and a pharmaceutically acceptable carrier or diluent.

For these indications the appropriate dosage will, of course, vary depending upon, for example, the compound of the invention employed, the host, the mode of administration and the nature and severity of the condition being treated. However, in general, satisfactory results in animals are indicated to be obtained at daily dosages to achieve a blood concentration of from 20 to 2,000 nmol/L, preferably at daily dosages of 60 to 600 nmol/L.

The proteins of the invention may be administered by any conventional route, in particular enterally or parenterally, e.g. in the form of injectable solutions or suspensions.

The protein of the SEQ ID NO:1 is the preferred compound.

The present invention provides pharmaceutical compositions comprising compounds of the invention in association with at least one pharmaceutical carrier or diluent. Such compositions may be manufactured in conventional manner. See Remington's Pharmaceutical Science, 15$^{th}$ ed. Mack Publishing Company, Easton, Pa. (1980).

In another aspect of this invention, there is provided DNA sequences, vectors containing these sequences, cells containing said vectors, methods of recombinantly producing proteins and antibodies to the proteins of this invention. Also provided are isolated and/or recombinant DNA sequences (e.g., genomic or cDNA) coding for a protein which inhibits collagen-induced aggregation of human platelets. In a still further aspect, the invention provides recombinantly-produced proteins of this invention, e.g., having the sequences disclosed herein.

By the term "isolated" is meant that the inhibitor of this invention or other entity is present in a form separated from (purified from) components with which it is produced recombinantly or synthetically. All degrees of such isolation or purification are included generically. Preferred are degrees of isolation or purification whereby the inhibitor is useful for pharmaceutical purposes. For example, such degrees of isolation (e.g., activities or purities) can be routinely achieved by chromatographic techniques such as those used in the examples. Further purifications, e.g., to homogeneity, can be routinely achieved using conventional methods, such as those described in the following texts:

Methods of Enzymology, Volume 182, Guide to Protein Purification, ed. Murray P. Deutscher, Academic Press 1990;

Protein Purification Applications—A Practical Approach. ed. E.L.V. Harris and S. Angel, IRL-Press 1990;

Protein Purification, Principles and Practice, Robert Scopes, Springer-Verlag 1982; and Protein Purification, Principles, High Resolution Methods and Applications, ed. J.-C. Janson and L. Ryden, VCH publishers 1989.

Purity can be determined by any one of a number of routine methods, e.g., SDS polyacrylamide gel electrophoresis, analytical HPLC, etc. Purified inhibitor can be used to determine the amino acid sequence of the protein according to methods fully routine to one of ordinary skill in the art. Hewick, R. M. et al. (1981) J. Biol. Chem. 256, 7990–7997.

The amino acid sequence of the inhibitor of the present invention can be used to determine the sequence of suitable DNA probes, which can be used for finding new inhibitors, e.g., in other species. Such probes can be routinely synthesized, e.g., using automated DNA synthesizers, and screening of genomic or cDNA libraries is similarly routine for one of ordinary skill in the art. (See International Publication WO 90/07861, dated 26 Jul., 1990)

Therefore, the present invention also includes the DNA sequence corresponding to (coding for) both the DNA sequence (gene) for the Asp-Pallidipin, when isolated from the natural environment, e.g., in solution or on a vector, as well as muteins thereof. Methods for producing muteins are also routine and conventional for one of ordinary skill in the art, as are screening methods for testing the efficacy of such new proteins, e.g., as described herein.

Suitable muteins are those having at least a fraction, e.g., at least 5%, preferably at least 50%, most preferably at least 90% of the biological activity, e.g., collagen-induced platelet aggregation inhibition, of inhibitor as described herein.

Further the invention comprises a method of purification, wherein the purifying comprises the following consecutive steps:

(i) purifying by cation exchange chromatography;

(ii) purifying by anion exchange and (iii) purifying by size exclusion.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, if any, including EP 94250224.6, filed Sep. 2, 1994, are hereby incorporated by reference.

EXAMPLES

Example 1

Construction of the Expressing Vector

For construction of the inventive vector, coding for the Asp-Pallidipin, the following sense and antisense primers are employed:

p3:
5'-GCGATATCGCGACGAAGAATGCGAACTCATG-3' (NruI)

(SEQ ID NO:4); and p4:
5'-GCGATAGGATCCAAGCTTATTACTTCATGTTATC-3' (BamHI)

(SEQ ID NO:5)

are used.

PCR is for 8 cycles of 2 minutes at 94° C., 1 minute and 30 seconds at 42° C. and 2 minutes and 30 seconds at 72° C. using p3 and p4, as primer pairs and 1 μg template DNA. After gel purification and digestion with NruI and BamHI, the fragment is subcloned into pSB/pho. The plasmid is prepared by XmaI digestion followed by Mung bean treatment to blunt the 5' overhang and BamHI digestion.

The construct is checked by complete DNA sequencing of the inserted fragments using the dideoxy chain-termination method (F. Sanger et al. (1977) Proc. Nat'l. Acad. Sci. USA 74:5463–5467) and a sequencing kit with [$^{35}$S]dATP. Transformation of competent *E. coli* E15 with Pallidipin expression construct or empty plasmid (mock transformation) is carried out using standard methods (J. Sambrook et al. (1989) Molecular Cloning: A Laboratory Manual, Cold Spring Harbor Laboratory Press, Cold Spring Harbor, NY).

Example 2
Expression and Extraction of Asp-Pallidipin

For the pSB/pho plasmid (derived from pSB94; see J. Daum et al. (1989) Eur. J. Biochem. 185:347–354), overnight E15 cultures (S. J. Hayashi et al. (1964) J. Biol. Chem. 239:3091–3106) are diluted to 8% (v/v) in low phosphate medium and grown for 6 hours at 37° C. (A. Becker et al. (1994) Protein Expression and Purification 5:50–56). The bacteria are harvested after induction by centrifugation and resuspended in ¹⁄₁₀ volume of 50 mmol/L Tris-HCl (pH 8.0)/100 mmol/L NaCl. This preparation is frozen, thawed, and centrifuged, thus giving a first supernatant fraction (SN1). The bacterial pellet is resuspended and equilibrated for 10 min at room temperature in 0.5 mol/L saccharose before centrifugation. The supernatant (SN2) is kept for analysis, while the pellet is resuspended in ice-cold water supplemented with 1 mmol/L PMSF (phenylmethylsulfonylfluoride) and incubated for 10 min on ice. Following this osmotic shock, the cells are centrifuged and the supernatant (SN3) is collected. The pellet containing the cytoplasmic fraction (CF) is resuspended in 50 mmol/L Tris-HCl (pH 8.0)/100 mmol/L NaCl.

Example 3
Purification of Recombinant Asp-Pallidipin

The supernatant fraction containing the bulk of recombinant Asp-Pallidipin (SN1) is adjusted to pH 4.0 with acetic acid and applied to a cation exchange column (Mono S, Pharmacia) using an FPLC system. After washing with a gradient of 0 to 500 mmol/L NaCl in sodium acetate pH 4.0, elution of Asp-Pallidipin is achieved with 20 mmol/L NaPi, pH 7.0. Eluted fractions containing Asp-Pallidipin, as judged by SDS-polyacrylamide gel electrophoresis (PAGE) and immunoblotting, are pooled, adjusted to pH 8.0 and applied to an anion exchange column (Fractogel-EMD-TMAE 650, Merck). Elution of Asp-Pallidipin is achieved with a gradient of 0 to 1 mol/L NaCl in 20 mmol/L sodium acetate pH 8.4. For the final purification, eluent fractions containing Asp-Pallidipin are pooled, concentrated in the Seed-Vac (Bachofer) and subjected to size exclusion chromatography using Superose 12 (Pharmacia).

Example 4
Platelet Aggregation Assay

The assay is carried out essentially as described in the publication of C. Noeske-Jungblut (C. Noeske-Jungblut (1994) J. Biol. Chem. 269:5050–5053). Briefly, human blood is collected into ⅙ volume 71 mmol/L citric acid/85 mmol/L trisodium citrate/111 mmol/L glucose. Platelet-rich plasma is obtained by centrifugation at 135 g for 20 min. Asp-Pallidipin is incubated with 500 μl platelet-rich plasma for 1 min at 37° C. before the addition of collagen (2 μg/ml). The aggregation is monitored using a Micron aggregometer and the maximum value is determined. The $IC_{50}$ has a value of about 50 nM. A significant difference between the compounds with or without Asp in the first position cannot be seen.

The biological activity and the yield of Asp-Pallidipin purified from the periplasmic space of *E. coli* is determined. Platelet-rich plasma is incubated with Asp-Pallidipin and controls. Aggregation is induced by adding collagen. Wild-type Pallidipin purified from saliva is used as a positive control. Further some other constructs are used as controls, showing the advantage of the inventive Asp-Pallidipin. The protein of the invention and the controls show different yields (Table 2).

TABLE 2

| Strain | Yield |
| --- | --- |
| recombinant Pallidipin | 461 μg |
| recombinant arginyl-Pallidipin | 298 μg |
| recombinant aspartyl-Pallidipin | 864 μg |

Example 5
The adhesion of tumor cells to collagen is decreased in the presence of the protein of the invention The protein of the invention inhibits the adhesion of tumor cells to a collagen matrix. Therefore, migrating tumor cells can be prevented partially or completely from settling down in organs or blood vessels, when the protein of the invention is within the blood or the plasma of the patient.

MTLn3 cells (rat mammary tumor cells) are labelled with $^{51}$Cr. A well plate is coated with collagen (type III) at 4° C. overnight. 2·10$^4$ labelled cells in 500 μl DMEM F12 medium, 20 mmol/L Hepes, 1 mmol/L bicarbonate, 1% BSA are first incubated with 0,2,5 or 10 μl protein of the invention ("Superose Pool", 0.5 mg protein/ml) respectively for 10 min at 37° C. Then this suspension is transferred to a collagen-coated well and incubated for 2 h at 37° C. Thereafter, the wells are washed and the adherent cells are removed with 1 mol/L NaOH. The radioactivity of the adherent cells is counted.

TABLE 3

| amount of the inhibitor added μl | cell attachment (cpm) |
| --- | --- |
| 0 | 2215 |
| 2 | 2071 |
| 5 | 1608 |
| 10 | 1081 |

Example 6
Antibody production

About 100 μg of the inhibitor purified according to the examples are added to 0.5 ml of complete Freund's adjuvant and the emulsion is injected s.c. into a rabbit. After 2 weeks a second injection is given consisting of about 80 μg purified inhibitor and 0.5 ml incomplete Freund's adjuvant. After the injection, several samples of serum are taken to check the production of specific antibodies. They are assayed in a Western blot. 20 ng of the purified inhibitor is applied on a 12.5% SDS-polyacrylamide gel and the electrophoresis, blotting and detection are done according to standard methods described by E. Harlowe, D. Lane, (1988) Antibodies: a laboratory manual, Cold Spring Harbor Laboratory (dilution of the test serum 1:500, goat anti-rabbit peroxidase conjugated IgG as second antibody, detection with the ECL-kit from Amersham International, Amersham, UK). The blot shows that the antiserum specifically reacts with the purified inhibitor.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

---

We claim:

1. A method of producing a recombinant Pallidipin protein (Asp-Pallidipin), wherein the Asp-Pallidipin inhibits collagen-induced platelet aggregation of mammalian platelets, and wherein the Asp-Pallidipin comprises:
   (i) a protein (Pallidipin) selected from the group of Pallidipin proteins, and
   (ii) the amino acid aspartic acid,
   wherein the aspartic acid is connected by a peptide bond with the N-terminal end of the Pallidipin;
whereby the Asp-Pallidipin has an amino acid sequence selected from:
   a) the sequences indicated in
      aa) SEQ ID NO:1;
      bb) SEQ ID NO:2; or
      cc) SEQ ID NO:3; or
   b) an allelic variant of the sequences of any of the SEQ ID NOS:1 to 3, or
   c) a protein according to any of the SEQ ID NOS: 1 to 3 or a variant mentioned under b), having a post-translational modification which does not substantially affect the platelet aggregation inhibitory activity of the mature protein;
comprising the steps of:
   aa) transfecting at least one bacterium with an appropriate vector, wherein the vector comprises an operable linkage of:
      (i) a first DNA or cDNA molecule, encoding recombinant Asp-Pallidipin,
      (ii) a second DNA molecule, encoding a suitable signal peptide sequence, and
      (iii) a suitable promoter;
      whereby, upon expression, the preprotein comprising the signal peptide and Asp-Pallidipin is cleaved so that the amino acid aspartic acid is in the position +1 of the amino acid sequence of the mature Asp-Pallidipin,
   bb) expressing the preprotein comprising the Asp-Pallidipin and the signal peptide sequence;
   cc) transporting the Asp-Pallidipin from the cytoplasm of the bacterium to the periplasm, whereby cleavage of the preprotein by at least one protease during transport produces the mature Asp-Pallidipin,
   dd) isolating the Asp-Pallidipin by extracting the periplasm, and
   ee) purifying the Asp-Pallidipin.

2. A process according to claim 1, wherein the DNA encoding the signal sequence codes for the signal sequence of alkaline phosphatase (APase).

3. A process according to claim 1, wherein the bacterium is *E. coli*.

4. A method of treatment of atherosclerotic or thrombotic disease or for preventing reocclusion after treatment of myocardial infarction, comprising administering to a patient in need of such treatment an effective amount of an Asp-Pallidipin produced by a method of claim 1.

5. A method of treatment of cancer with metastatic tumor cells, comprising administering to a patient in need of such treatment an effective amount of Asp-Pallidipin produced by a method of claim 1.

6. A process of purification of an Asp-Pallidipin produced according to claim 1, wherein the purifying comprises the following consecutive steps:
   (i) purifying by cation exchange chromatography;
   (ii) purifying by anion exchange; and
   (iii) purifying by size exclusion.

7. A method of producing a recombinant Pallidipin protein (Asp-Pallidipin), wherein the Asp-Pallidipin inhibits the collagen-induced platelet aggregation of mammalian platelets, and wherein the Asp-Pallidipin comprises:

(i) a protein (Pallidipin) selected from the group of Pallidipin proteins, and (ii) the amino acid aspartic acid, wherein the aspartic acid is connected by a peptide bond with the N-terminal end of Pallidipin;

whereby the Asp-Pallidipin has an amino acid sequence selected from:

a) the sequences indicated in
   aa) SEQ ID NO:1;
   bb) SEQ ID NO:2; or
   cc) SEQ ID NO:3; or b) an allelic variant of the sequences in any of the SEQ ID NOS: 1 to 3, or c) a protein according to any of the SEQ ID NOS: 1 to 3 or a variant mentioned under b), having a post-translational modification which does not substantially affect the platelet aggregation inhibitory activity of the mature protein;

comprising:

culturing a bacterium transfected with an appropriate vector, wherein the vector comprises an operable linkage of:

(i) a first DNA or cDNA molecule, encoding a recombinant Asp-Pallidipin, (ii) a second DNA molecule, encoding a suitable signal peptide sequence, and (iii) a suitable promoter;

whereby, upon expression, the preprotein comprising the signal peptide and Asp-Pallidipin is cleaved so that the amino acid aspartic acid is in the position +1 of the amino acid sequence of the mature Asp-Pallidipin, under conditions whereby (A) the preprotein comprising the Asp-Pallidipin and the signal peptide sequence is expressed, and (B) the Asp-Pallidipin is transported from the cytoplasm of the bacterium to the periplasm, whereby cleavage of the preprotein by at least one protease during transport produces the mature Asp-Pallidipin, and purifying the thus-produced Asp-Pallidipin from the periplasm.

8. A recombinant protein Asp-Pallidipin, wherein the Asp-Pallidipin inhibits collagen-induced platelet aggregation of mammalian platelets, and wherein the Asp-Pallidipin comprises:

(i) a protein (Pallidipin) selected from the group of Pallidipin proteins, and (ii) the amino acid aspartic acid, wherein the aspartic acid is connected by a peptide bond with the N-terminal end of the Pallidipin;

whereby the Asp-Pallidipin has an amino acid sequence selected from:

a) the sequences indicated in
   aa) SEQ ID NO:1;
   bb) SEQ ID NO:2; or
   cc) SEQ ID NO:3; or b) an allelic variant of the sequences in any of the SEQ ID NOS: 1 to 3, or c) a protein according to any of the SEQ ID NOS: 1 to 3 or a variant mentioned under b), having a post-translational modification which does not substantially affect the platelet aggregation inhibitory activity of the mature protein.

9. A pharmaceutical composition comprising an effective amount of an Asp-Pallidipin according to claim 8 in association with a pharmaceutically acceptable diluent or carrier.

10. A method of treatment of atherosclerotic or thrombotic disease or for preventing reocclusion after treatment of myocardial infarction, comprising administering to a patient in need of such treatment an effective amount of an Asp-Pallidipin of claim 8.

11. A recombinant protein Asp-Pallidipin, wherein the Asp-Pallidipin inhibits collagen-induced platelet aggregation of mammalian platelets, and wherein the Asp-Pallidipin comprises (i) a protein (Pallidipin) selected from the group of Pallidipin proteins, and (ii) the amino acid aspartic acid, wherein the aspartic acid is connected by a peptide bond with the N-terminal end of the Pallidipin;

whereby the Asp-Pallidipin has an amino acid sequencer selected from:

a) the sequences indicated in
   aa) SEQ ID NO:1;
   bb) SEQ ID NO:2; or
   cc) SEQ ID NO:3; or b) an allelic variant of the sequences in any of the SEQ ID NOS: 1 to 3, or c) a protein according to any of the SEQ ID NOS: 1 to 3 or a variant mentioned under b), having a post-translational modification which does not substantially affect the platelet aggregation inhibitory activity of the mature protein;

wherein the Asp-Pallidipin is produced by a process comprising the steps:

aa) transfecting at least one bacterium with an appropriate vector, wherein the vector comprises an operable linkage of:

(i) a first DNA or cDNA molecule, encoding recombinant Asp-Pallidipin, (ii) a second DNA molecule, encoding a suitable signal peptide sequence, and (iii) a suitable promoter;

whereby, upon expression, the preprotein comprising the signal peptide and Asp-Pallidipin is cleaved so that the amino acid aspartic acid is in the position +1 of the amino acid sequence of the mature Asp-Pallidipin, bb) expressing the preprotein comprising the Asp-Pallidipin and the signal peptide sequence;

cc) transporting the Asp-Pallidipin from the cytoplasm of the bacterium to the periplasm, whereby cleavage of the preprotein by at least one protease during transport produces the mature Asp-Pallidipin, dd) isolating the Asp-Pallidipin by extracting the periplasm, and ee) purifying the Asp-Pallidipin.

12. A Asp-Pallidipin according to claim 11, wherein the DNA encoding the signal peptide sequence encodes a signal sequence of alkaline phosphatase (APase).

13. A recombinant protein Asp-Pallidipin, wherein the Asp-Pallidipin inhibits collagen-induced platelet aggregation of mammalian platelets, and wherein the Asp-Pallidipin comprises:

(i) a protein (Pallidipin) selected from the group of Pallidipin proteins, and (ii) the amino acid aspartic acid, wherein the aspartic acid is connected by a peptide bond with the N-terminal end of Pallidipin;

whereby the Asp-Pallidipin has an amino acid sequence selected from:

a) the sequences indicated in
   aa) SEQ ID NO:1;
   bb) SEQ ID NO:2; or
   cc) SEQ ID NO:3; or
b) an allelic variant of the sequences in any of the SEQ ID NOS: 1 to 3, or
c) a protein according to any of the SEQ ID NOS: 1 to 3 or a variant mentioned under b), having a post-translational modification which does not substantially affect the platelet aggregation inhibitory activity of the mature protein;

wherein the Asp-Pallidipin is produced by a process comprising:

culturing a bacterium transfected with an appropriate vector, wherein the vector comprises an operable linkage of:

(i) a first DNA or cDNA molecule, encoding a recombinant Asp-Pallidipin, (ii) a second DNA molecule, encoding a suitable signal peptide sequence, and (iii) a suitable promoter;

whereby, upon expression, the preprotein comprising the signal peptide and Asp-Pallidipin is cleaved so that the amino acid aspartic acid is in the position +1 of the amino acid sequence of the mature Asp-Pallidipin, under conditions whereby (A) the preprotein comprising the Asp-Pallidipin and the signal peptide sequence is expressed, and (B) the Asp-Pallidipin is transported from the cytoplasm of the bacterium to the periplasm, whereby cleavage of the preprotein by at least one protease during transport produces the mature Asp-Pallidipin, and purifying the Asp-Pallidipin, from the periplasm.

14. A recombinant vector comprising an operable linkage of:

(i) a first DNA or cDNA molecule, encoding a recombinant Asp-Pallidipin, (ii) a second DNA molecule, encoding a suitable signal peptide sequence, and (iii) a suitable promoter;

whereby, upon expression in a suitable bacterial host, the preprotein comprising the signal peptide and Asp-Pallidipin is cleaved so that the amino acid aspartic acid is in the position +1 of the amino acid sequence of the mature Asp-Pallidipin.

15. A recombinant vector of claim 14, wherein the DNA or cDNA molecule encodes an Asp-Pallidipin having an amino acid sequence selected from:

a) the sequences indicated in
   aa) SEQ ID NO:1;
   bb) SEQ ID NO:2; or
   cc) SEQ ID NO:3; or
b) an allelic variant of the sequences in any of the SEQ ID NOS: 1 to 3.

16. A bacterial host transformed with a vector of claim 14.

17. A bacterial host of claim 16, which is an *E coli.*

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 172 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO: 1:

```
Asp  Glu  Glu  Cys  Glu  Leu  Met  Pro  Pro  Gly  Asp  Asn  Phe  Asp  Leu  Glu
1                   5                        10                       15

Lys  Tyr  Phe  Ser  Ile  Pro  His  Val  Tyr  Val  Thr  His  Ser  Arg  Asn  Gly
               20                       25                       30

Pro  Lys  Glu  Gln  Val  Cys  Arg  Glu  Tyr  Lys  Thr  Thr  Lys  Asn  Ser  Asp
          35                        40                       45

Gly  Thr  Thr  Thr  Thr  Leu  Val  Thr  Ser  Asp  Tyr  Lys  Thr  Gly  Gly
     50                   55                       60

Lys  Pro  Tyr  His  Ser  Glu  Leu  Lys  Cys  Thr  Asn  Thr  Pro  Lys  Ser  Gly
65                       70                       75                            80

Gly  Lys  Gly  Gln  Phe  Ser  Val  Glu  Cys  Glu  Val  Pro  Asn  Gly  Asn  Gly
                    85                        90                            95

Gly  Lys  Lys  Lys  Ile  His  Val  Glu  Thr  Ser  Val  Ile  Ala  Thr  Asp  Tyr
               100                      105                      110

Lys  Asn  Tyr  Ala  Leu  Leu  Gln  Ser  Cys  Thr  Lys  Thr  Glu  Ser  Gly  Ile
          115                      120                      125

Ala  Asp  Asp  Val  Leu  Leu  Leu  Gln  Thr  Lys  Lys  Glu  Gly  Val  Asp  Pro
     130                      135                      140

Gly  Val  Thr  Ser  Val  Leu  Lys  Ser  Val  Asn  Trp  Ser  Leu  Asp  Asp  Trp
145                      150                      155                           160

Phe  Ser  Arg  Ser  Lys  Val  Asn  Cys  Asp  Asn  Met  Lys
               165                      170
```

( 2 ) INFORMATION FOR SEQ ID NO: 2:

( i ) SEQUENCE CHARACTERISTICS:
        ( A ) LENGTH: 171 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO: 2:

```
Asp  Glu  Glu  Cys  Glu  Leu  Met  Pro  Pro  Gly  Asp  Asn  Phe  Asp  Leu  Glu
1                   5                        10                       15
```

|  |  |  |  |  |  |  |  |  |  |  |  |  |  |  |
|---|---|---|---|---|---|---|---|---|---|---|---|---|---|---|
| Lys | Tyr | Phe | Ser<br>20 | Ile | Pro | His | Val<br>25 | Val | Thr | His | Ser | Arg<br>30 | Asn | Gly |
| Pro | Lys | Glu<br>35 | Gln | Val | Cys | Arg | Glu<br>40 | Tyr | Lys | Thr | Thr | Lys<br>45 | Asn | Ser | Asp |
| Gly | Thr<br>50 | Thr | Thr | Thr | Leu | Val<br>55 | Thr | Ser | Asp | Tyr | Lys<br>60 | Thr | Gly | Gly | Lys |
| Pro<br>65 | Tyr | His | Ser | Glu | Leu<br>70 | Lys | Cys | Thr | Asn | Thr<br>75 | Pro | Lys | Ser | Gly | Val<br>80 |
| Lys | Gly | Gln | Phe | Ser<br>85 | Val | Glu | Cys | Glu | Val<br>90 | Pro | Asn | Gly | Asn | Gly<br>95 | Gly |
| Lys | Lys | Lys | Ile | His<br>100 | Val | Glu | Thr | Ser<br>105 | Val | Ile | Ala | Thr | Asp<br>110 | Tyr | Lys |
| Asn | Tyr | Ala | Leu<br>115 | Leu | Gln | Ser | Cys<br>120 | Thr | Lys | Thr | Glu | Ser<br>125 | Gly | Ile | Ala |
| Asp | Asp<br>130 | Val | Leu | Leu | Leu | Gln<br>135 | Thr | Lys | Lys | Glu | Gly<br>140 | Val | Asp | Pro | Gly |
| Val<br>145 | Thr | Ser | Val | Leu | Lys<br>150 | Ser | Val | Asn | Trp | Ser<br>155 | Leu | Asp | Asp | Trp | Phe<br>160 |
| Ser | Arg | Ser | Lys | Val<br>165 | Asn | Cys | Asp | Asn | Met<br>170 | Lys |

( 2 ) INFORMATION FOR SEQ ID NO: 3:

( i ) SEQUENCE CHARACTERISTICS:
        ( A ) LENGTH: 172 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO: 3:

|  |  |  |  |  |  |  |  |  |  |  |  |  |  |  |  |
|---|---|---|---|---|---|---|---|---|---|---|---|---|---|---|---|
| Asp<br>1 | Glu | Glu | Cys | Glu<br>5 | Leu | Met | Pro | Pro | Gly<br>10 | Asp | Asn | Phe | Asp | Leu<br>15 | Glu |
| Lys | Tyr | Phe | Ser<br>20 | Ile | Pro | His | Val<br>25 | Tyr | Val | Thr | His | Ser | Arg<br>30 | Asn | Gly |
| Pro | Lys | Glu<br>35 | Gln | Val | Cys | Arg | Glu<br>40 | Tyr | Lys | Thr | Thr | Lys<br>45 | Asn | Ser | Asp |
| Gly | Thr<br>50 | Thr | Thr | Thr | Thr | Leu<br>55 | Val | Thr | Ser | Asp | Tyr<br>60 | Lys | Thr | Gly | Gly |
| Lys<br>65 | Pro | Tyr | His | Ser | Glu<br>70 | Leu | Lys | Cys | Thr | Asn<br>75 | Thr | Gln | Lys | Ser | Gly<br>80 |
| Gly | Lys | Gly | Gln | Phe<br>85 | Ser | Val | Glu | Cys | Glu<br>90 | Val | Pro | Asn | Gly | Asn<br>95 | Gly |
| Gly | Lys | Lys | Lys<br>100 | Ile | His | Val | Glu | Thr<br>105 | Ser | Val | Ile | Ala | Thr<br>110 | Asp | Tyr |
| Lys | Asn | Tyr | Ala<br>115 | Leu | Leu | Gln | Ser<br>120 | Cys | Thr | Lys | Thr | Glu<br>125 | Ser | Gly | Ile |
| Ala | Asp | Asp<br>130 | Val | Leu | Leu | Leu | Gln<br>135 | Thr | Lys | Lys | Glu | Gly<br>140 | Val | Asp | Pro |
| Gly<br>145 | Val | Thr | Ser | Val | Leu<br>150 | Lys | Ser | Val | Asn | Trp<br>155 | Ser | Leu | Asp | Asp | Trp<br>160 |
| Phe | Ser | Arg | Ser | Lys<br>165 | Val | Asn | Cys | Asp | Asn<br>170 | Met | Lys |

( 2 ) INFORMATION FOR SEQ ID NO: 4:

( i ) SEQUENCE CHARACTERISTICS:
   ( A ) LENGTH: 31 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "sense primer"

( i i i ) HYPOTHETICAL: NO ( i v ) ANTI-SENSE: NO ( x i ) SEQUENCE DESCRIPTION: SEQ ID NO: 4:

GCGATATCGC GACGAAGAAT GCGAACTCAT G                                      3 1

( 2 ) INFORMATION FOR SEQ ID NO: 5:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "antisense primer"

( i i i ) HYPOTHETICAL: NO ( i v ) ANTI-SENSE: YES ( x i ) SEQUENCE DESCRIPTION: SEQ ID NO: 5:

GCGATAGGAT CCAAGCTTAT TACTTCATGT TATC                                   3 4